US010256086B2

(12) United States Patent
Fries et al.

(10) Patent No.: US 10,256,086 B2
(45) Date of Patent: *Apr. 9, 2019

(54) SYSTEMS AND METHODS FOR BUBBLE BASED ION SOURCES

(71) Applicant: University of South Florida, Tampa, FL (US)

(72) Inventors: David P. Fries, St. Petersburg, FL (US); William Abbott, St. Petersburg, FL (US); Bo Yang, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,825

(22) Filed: Sep. 1, 2017

(65) Prior Publication Data

US 2018/0012748 A1 Jan. 11, 2018

Related U.S. Application Data

(63) Continuation of application No. 15/147,204, filed on May 5, 2016, now Pat. No. 9,812,312.

(60) Provisional application No. 62/156,963, filed on May 5, 2015.

(51) Int. Cl.
| *H01J 49/16* | (2006.01) |
| *G01N 27/62* | (2006.01) |
| *H01J 49/06* | (2006.01) |
| *H01J 49/10* | (2006.01) |
| *H01J 49/04* | (2006.01) |

(52) U.S. Cl.
CPC .......... *H01J 49/10* (2013.01); *H01J 49/0431* (2013.01); *H01J 49/16* (2013.01); *G01N 27/622* (2013.01)

(58) Field of Classification Search
CPC ....... H01J 49/16; H01J 49/062; G01N 27/622
USPC .... 250/423 R, 424, 288; 315/111.01, 111.81
See application file for complete search history.

(56) References Cited

U.S. PATENT DOCUMENTS

| 2,956,169 A | 12/1956 | King |
| 3,462,633 A | 8/1969 | McCoy |
| 3,558,688 A | 1/1971 | Drinkard et al. |
| 5,175,359 A | 12/1992 | Fried |

(Continued)

FOREIGN PATENT DOCUMENTS

CN 201921771 U 1/2011

OTHER PUBLICATIONS

Ikezi, H. and Taylor, R.J., "Ion-Burst Excited by a Grid in a Plasma," Journal of Applied Physics, 41, 738-742 (1970), DOI:http://dx.doi.org/10/1053/1.1658741.

(Continued)

*Primary Examiner* — Nicole M Ippolito
(74) *Attorney, Agent, or Firm* — Thomas | Horstemeyer, LLP

(57) ABSTRACT

The present disclosure describes embodiments directed to a bubble based ion source system comprising an ion source configured to generate a plurality of ions, an ion channel, an electrode, and/or any other components. The ion source can include a container at least partially comprising a solvent or solution, a bubble generator coupled to the container configured to generate a plurality of bubbles within the solvent, and/or any other component. The ion channel can receive ions that are generated based on solvent from the bubbles.

20 Claims, 18 Drawing Sheets

(56) References Cited

U.S. PATENT DOCUMENTS

| | | | |
|---|---|---|---|
| 5,412,208 | A | 5/1995 | Covey et al. |
| 5,943,075 | A | 8/1999 | Lee et al. |
| 7,204,431 | B2 | 4/2007 | Li et al. |
| 9,812,312 | B2 * | 11/2017 | Fries .................. H01J 49/16 |
| 2006/0285108 | A1 | 12/2006 | Morrisroe |
| 2011/0049354 | A1 | 3/2011 | Englmann et al. |

OTHER PUBLICATIONS

Yoshimura, S., Ichiki, R., Shindo, M., and Kawai, Y., Ion-Burst Method for Postive and Negative Ion Species Measurements, Thin Solid Films, vol. 390, Issues 1-2, Jun. 30, 2001, pp. 212-216, ISSN 0040-6090, http://dx.doi.org/10.1016/S0040-6090(01)00951-8.

Corr, Jay J. and Anacleto, Joseph F., "Analysis of Inorganic Species by Capillary Electrophoresis-Mass Spectrometry and Ion Exchange Chromatography-Mass Spectrometry Using an Ion Spray Source," Analytical Chemistry 1996 68 (13), 2155-2163.

Kanu, Abu B., et al. "Ion Mobility-Mass Spectrometry." Journal of Mass Spectrometry 43.1 (2008): 1-22.

Blanchard, Duncan C. "The Size and Height to Which Jet Drops Are Ejected From Bursting Bubbles in Seawater." Journal of Geophysical Research: Oceans 94.C8 (1989): 10999-11002.

Feng, Xiao, and George R. Agnes. "Single Isolated Droplets With Net Charge as a Source of Ions." Journal of the American Society for Mass Spectrometry 11.5 (2000): 393-399.

Davis, E. "A Button-Electrode Levitation Chamger for the Study of Ice Crystal Growth Under Atmospherc Conditions." College of Earth and Mineral Sciences 2010. Penn State University, p. 68.

Li, Xiaoxu, et al. "Ion Trap Array Mass Analyzer: Structure and Performance." Analytical chemistry 81.12 (2009): 4840-4846.

Blanchard, Duncan C., and Lawrence D. Syzdek. "Apparatus to Determine the Efficiency of Transfer of Bacteria From a Bursting Bubble to the Jet Drops." Limnology and oceanography 35.1 (1990):136-143.

Blanchard, D. C., and A. H. Woodcock. "Bubble Formation and Modification in the Sea and Its Meteorological Significance." Tellus 9.2 (1957): 145-158.

Blanchard, Duncan C., and Lawrence D. Syzdek. "Electrostatic Collection of Jet and Film Drops." Limnology and Oceanography 20.5 (1975): 762-774.

Tona, Masahide, and Masahiro Kimura. "Parallel-Plate Ion Trap Useful for Optical Studies of Microparticles." Review of scientific instruments 75/ (2004): 2276-2279.

Parkinson, Luke, et al. "The Terminal Rise Velocity of 10-100 MM Diameter Bubbles in Water." Journal of colloid and interface science 322.1 (2008): 168-172.

Shew, Woodrow-L., Sebastien Poncet, and Jean François Pinton. "Force Measurements on Rising Bubbles." Journal of Fluid Mechanics 569 (2006): 51.

Willoughby, Ross, David Fries, and Ed Sheehan. "Electro-Fluidic Based Micro Ion Optical Ion Selective Apertures Using PCBMEMS Technology." Industrial Technology (ICIT), 2010 IEEE International conference on. IEEE, 2010.

* cited by examiner

SYSTEMS AND METHODS FOR BUBBLE BASED ION SOURCES

CROSS-REFERENCE TO RELATED APPLICATIONS

This application is a continuation of, claims the benefit of, and priority to U.S. patent application Ser. No. 15/147,204, entitled "SYSTEMS AND METHODS FOR BUBBLE BASED ION SOURCES," filed on May 5, 2016, and claims priority to, and the benefit of U.S. provisional application entitled "SYSTEMS AND METHODS FOR BUBBLE BASED ION SOURCES" having Ser. No. 62/156,963, filed May 5, 2015 which are hereby incorporated by reference in their entireties.

BACKGROUND

Certain traditional methods and systems directed to ion generation can involve the application of high voltage at a low current. For example, electrospray ionization can involve applying a high voltage on a flow of liquid that is directed to a small opening in a vacuum system, where droplets are de-solvated such that ions are ejected from the droplets and accelerated into a mass analyzer. However, the use of an electrospray for ionization can be limited in that a high voltage is necessary. Moreover, the current capacity can also be limited due to the limited throughput available from the flow of the liquid through the electrospray.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1:
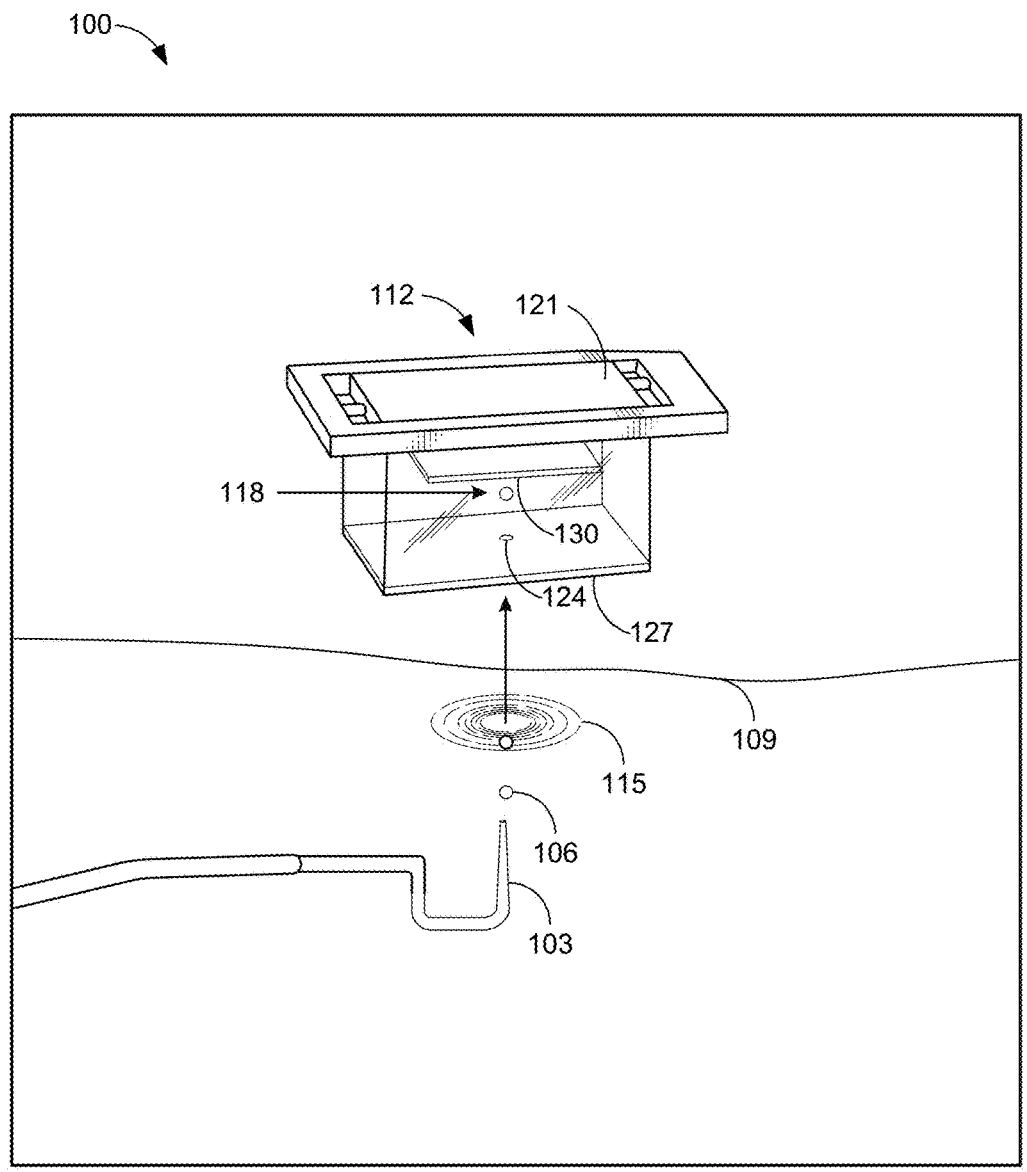
FIGS. 1 and 2 are drawings of examples of a bubble based ion source system.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

In the following paragraphs, the embodiments are described in further detail by way of example with reference to the attached drawings. In the description, well known components, methods, and/or processing techniques are omitted or briefly described so as not to obscure the embodiments. As used herein, the "present invention" refers to any one of the embodiments of the invention described herein and any equivalents. Furthermore, reference to various feature(s) of the "present invention" is not to suggest that all embodiments must include the referenced feature(s).

The embodiments described herein are not limited in application to the details set forth in the following description or illustrated in the drawings. The invention is capable of other embodiments and of being practiced or carried out in various ways. Also, the phraseology and terminology used herein is for the purpose of description and should not be regarded as limiting. The use of "including," "comprising," or "having" and variations thereof herein is meant to encompass the items listed thereafter, additional items, and equivalents thereof. The terms "connected" and "coupled" are used broadly and encompass both direct and indirect connections and couplings. In addition, the terms "connected" and "coupled" are not limited to electrical, physical, or mechanical connections or couplings. Common numerals in figures represent the same or a similar element and further descriptions may be omitted.

The present disclosure describes embodiments directed to a bubble based ion source system including an ion source configured to generate a plurality of ions, a heat source positioned above the container, an ion channel comprising an aperture and a plurality of electrodes. The ion source further comprises a container at least partially comprising a solvent or solution, a bubble generator coupled to the container configured to generate a plurality of bubbles within the solvent. The heat source can be configured to evaporate at least a portion of the solvent from each of the bubbles leaving a plurality of ions. The ion channel can be configured to receive the ions through the aperture. The electrodes of the ion channel can also be configured to facilitate guiding the ion to an analyzer.

In one embodiment, the heat source can comprise at least one of an electrode, an infrared ray, or an infrared projection. In some embodiments, the bubble generator can be configured to inject air into the solvent to generate bubbles. In this regard, the bubble generator can comprise a tube structure to facilitate the passage of air into the solvent to generate the bubbles.

In one embodiment, the bubble based ion source system can comprise an electrode coupled to the ion channel to apply a voltage to the ion channel. In some embodiments, the ion channel can comprise a plurality of layers. Each layer can be applied a differed voltage depending on the configuration of the chamber and a desired field strength. The analyzer device can be at least one of an ion mobility spectrometer, a mass spectrometer, a charged particle deposition system, or a charge energy generation device In particular, the component parts of the bubble based ion source system can be at atmosphere and therefore the method of applying the bubble based ion source system can also be performed at atmosphere. In this regard, a method of generating ions using the bubble based ion source system can comprise generating a plurality of bubbles in a solvent, the bubbles rising to a surface of the solvent, evaporating at least a portion of the solvent from each of the bubbles via a heat source leaving a plurality of ions through an aperture of an ion channel, and applying a voltage to the ion channel to guide the ions to an analyzer, the voltage based at least in part on a configuration of the ion channel and a desired field strength, the ion channel comprising a plurality of layers.

In some embodiments, the bubble based ion source system can provide for low voltage and efficient ion generation and transportation to ion mobility spectrometers (MS), mass spectrometers (MS) analytical devices, charged particle deposition systems, and charge energy generation devices. The bursting of bubbles on a surface of water and the natural atomization process that occurs with that bursting can be a source of ions from a low voltage environment and at a high capacity over large areas.

Ion mobility mass spectrometry is an analytical chemistry technique for accurate determination of molecular weights, identification of chemical structures, and determination of the composition of mixtures and quantitative elemental analysis. In particular, MS can accurately determine the weights of molecules and determine the structure of molecules based on fragmentation patterns of the ions that are formed when the molecule is ionized.

Ion source based systems can comprise a sample introduction, a compound ionization, and any other necessary phases. The ion source based systems can utilize the bubble bursting ion source systems and methods disclosed herein. Molecule analytical systems can further comprise phases such as ion mobility separation, mass separation, and ion detection. The present disclosure describes embodiments related to the natural atomization process from bursting bubbles that generate ions which can be carried to ion based analytical, deposition, and/or charging systems.

With reference to FIG. 1, shown is a bubble based ion source system 100 for the measurement of electric charges on jet drops. The bubble based ion source system can include bubble generators 103, gas bubbles 106, a solution surface 109, and a chamber 112.

The gas bubble 106 can breach the solution surface 109 of the solution. The gas bubble 106 can burst when the gas bubble 106 breaches the solution surface 109. The bursting of the gas bubble 106 can generates a force that causes ripples 115 on the solution surface 109. The force from the gas bubble 106 bursting can also generate a jet drop 118.

The chamber 112 can include a heat source 121, an aperture 124 in a first plate 127, and a second plate 130. In some embodiments, the heat source 121 is omitted. The jet drops 118 can pass through one or more apertures 124 to enter the chamber 112. In one embodiment, the aperture 124 is a circular hole in the first plate 127 of the chamber 112. In some embodiments, multiple apertures 124 are positioned in a path of multiple bubble generators 103. The bubble generators 103 can be placed in an array to generate a larger volume of jet drops 118.

The aperture 124 can be in the form of other shape, such as ellipses, an elongated slit, rectangle, or other shapes. The chamber 112 can be positioned such that the aperture 124 is perpendicular to a path of the jet drop 118, such that the jet drop 118 can pass through the aperture 124.

The heat source 121 can be an infrared heating element configured to generate infrared heat. The heat source 121 can be an electrode, an infrared ray, an infrared projection, or another heat source. The jet drop 118 can enter the chamber 112 as a droplet, for example, a full volume liquid or bubble with a gas interior and liquid surrounding the gas. The heat source 121 can modulate the jet drop 118 and cause the liquid to evaporate to reduce the size of the jet drop 118. As an example, the jet drop 118 can be reduced by the heat source to large particles in the range of 100 microns to 100 millimeters, small particles in the range of 10 microns to less than 100 microns, and to charged molecules that are a nanometer or less in size.

The jet drop 118 can be transported at various sizes based on different embodiments of the present disclosure. In different embodiments, the jet drop 118 can be transported at a size of one or more of a droplet, large particles, small particles, charged molecules, or other sizes. The heat source 121 can supply the infrared heat to an interior of the chamber 112 to reduce the size of the jet drop 118. The heat source 121 can be positioned at an opposite side of the chamber 112 in comparison to the side of the chamber 112 containing the aperture 124. For example, the heat source 121 can be located on an upper side of the chamber 112 relative to a vertical z-axis.

The plates 127 and 130 can act as separator. In some embodiments, the plates 127 and 130 also act as an ion trap. In other embodiments, another pair of parallel plates act as an ion trap to transport the particle. The plates 127 and 130 can be substantially parallel to each other. The first plate 127 and the second plate 130 can have a high potential difference between each other. As an example, a positive terminal of a power source can be coupled to the first plate 127 and a negative terminal of the power source can be coupled to the second plate 130 to create the potential difference between the two plates 127 and 130. The high potential difference can create an electric field between the two plates 127 and 130. The jet drop 118 can be stabilized or levitated by the electric field between the two plates 127 and 130.

Once ionization has occurred, the ions can be transported and/or processed. For example, the bubble based ion source system 100 can include a spectrometer that receives the ions from the chamber 112. The ions can also be received by an ion trap. The trapped ions can be transported using a variety of transport mechanisms described herein. The trapped ions can be transported to a spectrometer for analysis. The trapped ions can also be transported for printing or processing in another way.

In one embodiment, the bubble based ion source system 100 is used with a beaker or vessel of a solution containing an analyte. In some embodiments, the bubble based ion source system 100 is used over a body of water, and the solution surface 109 is the surface of the body of water. The body of water can be a lake, an ocean, or another body of water. The bubble based ion source system 100 can be used to extract ions from the solution and move those ions, for example, the ions can be moved into a spectrometer.

Figure 2:
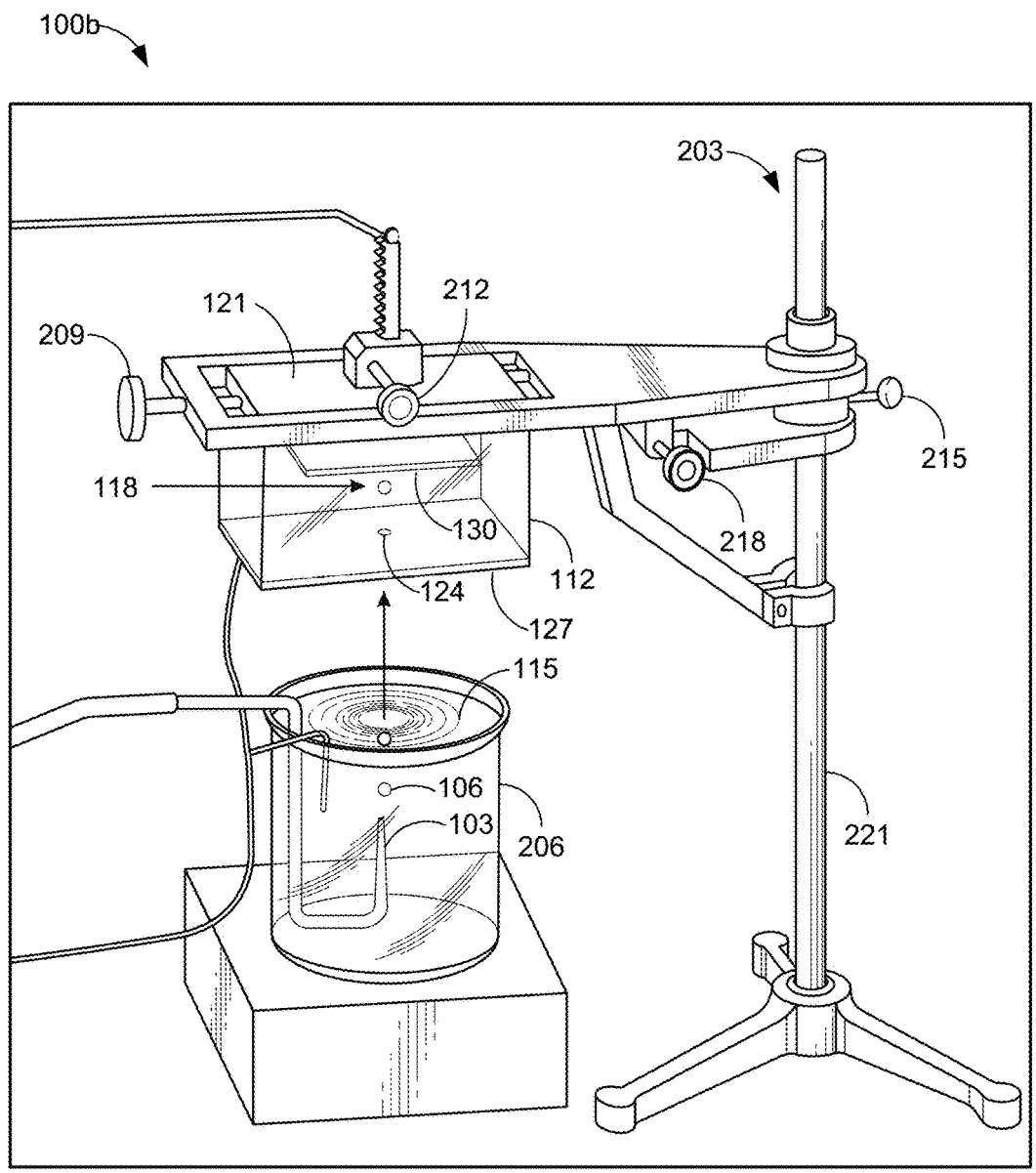

With reference to FIG. 2, shown is a bubble based ion source system 100b for the measurement of electric charges on jet drops. The bubble based ion source system 100b can include a supporting structure 203 and a vessel 206. The supporting structure 203 can include one or more adjustment knobs 209, 212, 215, and 218 and a stand 221. The supporting structure 203 can be configured to swivel such that an aperture 124 in the bottom chamber 112 can be lined up with the path of jet drops 118 that are expelled from the solution. The supporting structure can also be affixed in place by tightening adjustment knobs 209, 212, 215, and 218.

The vessel 206 can provide store the liquid within a hollow space of the vessel 206. A test solution can be added to the vessel, for example, an analyte. Gas bubbles 106 can be generated in the test solution to form jet drops 118. The jet drops 118 can be separated and ionized by the bubble based ion source system 100b. In some embodiments, the vessel 206 contains a buffer solution in addition to the test solution. The test solution can be floated on top of the buffer solution. The buffer solution can be water or another solution that does not interfere with the test solution. In some embodiments, the buffer solution has a lower density than the test solution to allow the test solution to float on top of the buffer solution.

An adjustment knob 209 can include a locking component and a rotational component. As an example, when the locking component of the adjustment knob 209 is in an unlocked position, the adjustment knob 209 can turn the upper plate that contains the heat source 121. The adjustment knob 209 can be restricted from turning when a locking component is in a locked position.

The heat source 121 can be affixed to the upper plate, such that turning the adjustment knob 209 turns the heat source 121. The heat source 121 can emit heat in a direction perpendicular to the upper plate. In some embodiments, the heat source 121 is separate from the upper plate, and turning the adjustment knob 209 does not change the direction of output of the heat source 121.

The adjustment knob 212 can raise and lower the second plate 130 relative to the chamber 112. The distance between the first plate 127 and the second plate 130 can be adjusted using the adjustment knob 212. In some embodiments, turning the adjustment knob 212 can require a user to overcome a resistance of the adjustment knob 212. The resistance can prevent the adjustment knob 212 moving when not in use. In other embodiments, the adjustment knob 212 includes a locking component similar to the adjustment knob 209 that prevents turning of the adjustment knob 212 when in a locked position.

The adjustment knob 215 can lock an arm of the stand 221. When the adjustment knob 215 is in an unlocked position, the arm can swivel around on the stand 221. When unlocked, the arm can also be raised and lowered on the stand 221. The adjustment knob 215 can have a threaded shaft that inserts into a threaded hole of the stand 221. Turning the adjustment knob 215 can cause the threaded shaft to contact the stand 221 to hold the arm in place.

Figure 3:
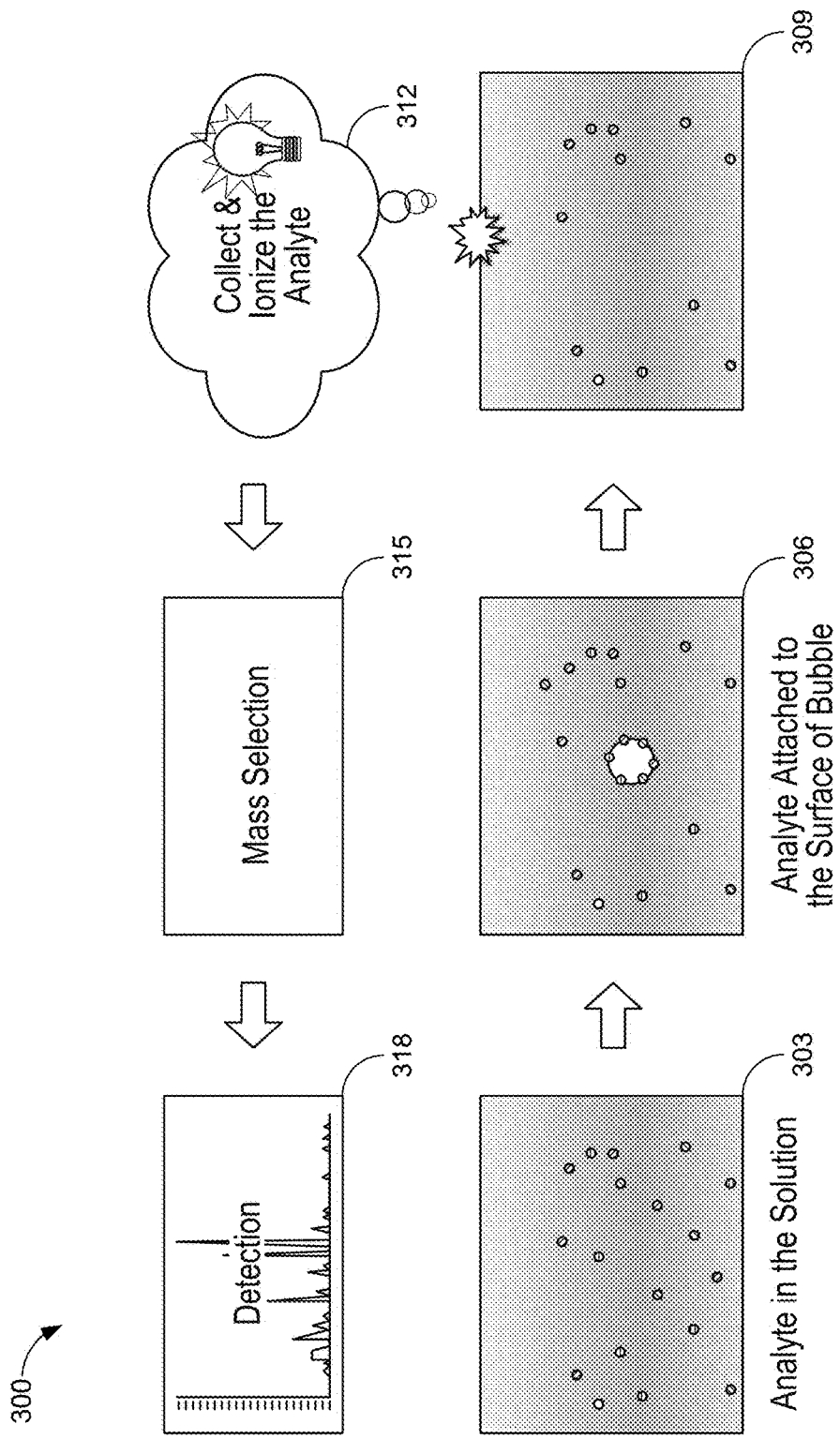
FIGS. 3, 4A, and 4B are diagrams illustrating examples of applications of a bubble based ion source system.

With reference to FIG. 3, shown is a diagram 300 illustrating an example of an application of a bubble based ion source system 100 according to various embodiments of the present disclosure. In particular, FIG. 3 illustrates a concept for ion sourcing via the bursting of bubbles for ion mobility or MS, for example.

At box 303, an analyte is within a solution. The analyte can preexist in the solution or can be added to the solution for the purpose of testing. As an example, the diagram 300 can illustrate the process for testing an analyte within a lake or ocean. The analyte can be naturally distributed within the solution.

At box 306, a bubble generator 103 can generate a gas bubble 106 within the solution. The analyte can attach to the surface of the gas bubble 106. As an example, as the gas bubble 106 can be propelled through the solution based on a disparity in the density of the gas bubble 106 in contrast to the solution. The gas bubble 106 can pass by the analyte in the solution. The analyte in the solution that encounters the gas bubble 106 can attach to the surface of the gas bubble 106. Multiple gas bubbles 106 can be generated in sequence. Further, multiple bubble generators 103 can be placed in an array to increase the number of jet drops 118 that are generated for subsequent use.

At box 309, the gas bubble 106 can breach the solution surface 109 of the sample. The gas bubble 106 can generate a force upon breaching the solution surface 109 and expel a jet drop 118. The jet drop 118 can include the analyte that attached to the gas bubble 106 in box 306. The jet drop 118 can also include gas from the gas bubble.

At element 312, the jet drop 118 can be collected and the analyte can be ionized. The jet drop 118 can enter the chamber 112 through an aperture 124. The chamber 112 can collect the jet drop 118 and ionize the analyte. In one embodiment, the analyte is ionized by the electric field created between the first plate 127 and a second plate 130. In another embodiment, the analyte is suspended by an electric field and ionized by a heat source 121.

At element 315, the mass of the ion can be selected. The mass selection can be performed by an ion trap. The mass selection can also be performed by a mass analyzer. The mass analyzer can be a quadrupole mass analyzer, a time of flight mass analyzer, a magnetic sector mass analyzer, an electrostatic sector mass analyzer, a quadrupole ion trap mass analyzer, an ion cyclotron resonance, or another mass analyzer. The mass of the ionized analyte can be selected by moving the ionized analyte in a desired direction for processing.

At box 318, the selected mass is detected. For example the mass can be moved into a sensing area of a spectrometer. The spectrometer can detect the ionized analyte in the selected mass.

Figure 4A:
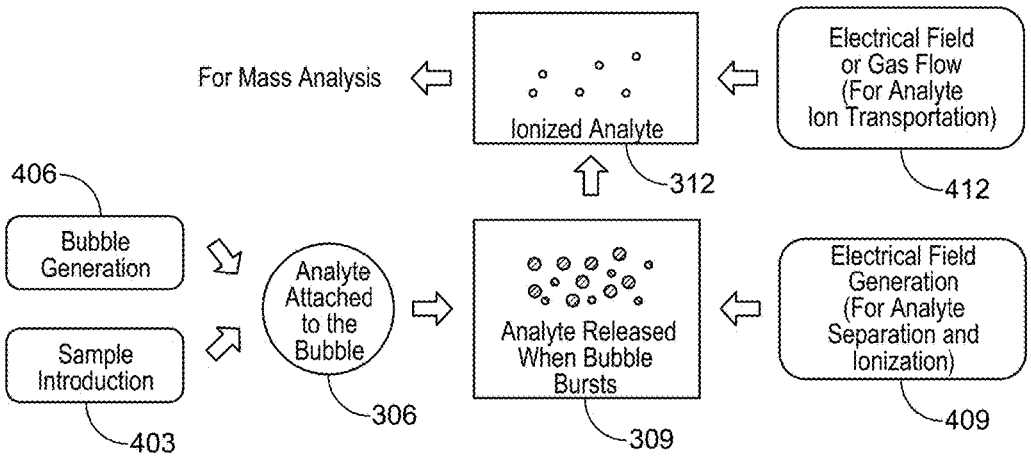
Figure 4B:
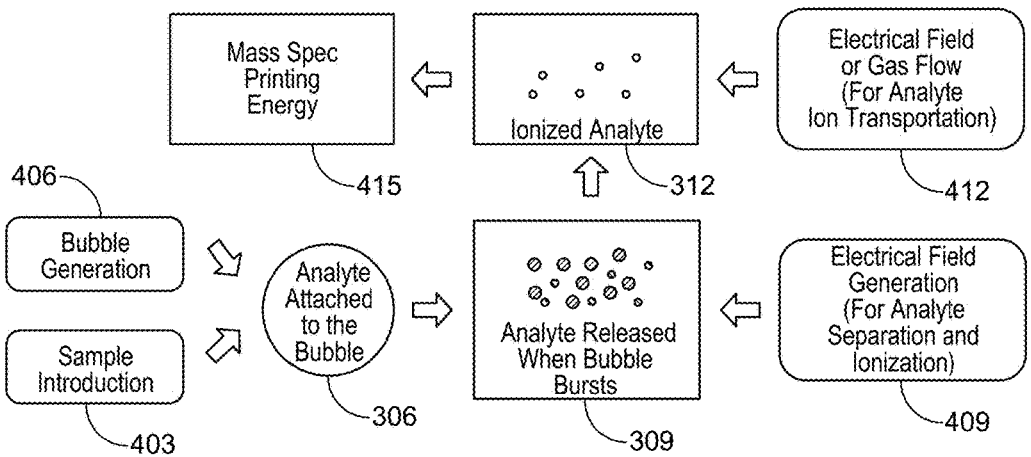

Similarly, in an analytical system example, FIGS. 4A and 4B describe the evolution of an analyte from solution to the atmosphere by absorption of at least a portion of the bubbles or the solution. When the bubble bursts, an ionized analyte can be released at the liquid/gas interface in the presence of an electric field.

Jet drops ejected from a solution by an air bubble that bursts at the surface of water can be stabilized or levitated by creating an electric field between two parallel plates with a high potential difference. In this regard, the gravitational force pulling the jet drop down will be balanced by the electric field pulling the opposite direction.

At box 403, a sample can be introduced into the solution. The sample can include the analyte. In one embodiment, the sample is the analyte. The sample can be poured into a vessel 206. In some embodiments, the sample is already within a solution.

At box 406, a bubble generator 103 can generate a gas bubble 106 within the solution. The bubble generator 103 can generate multiple gas bubbles 106 one after the other with a delay in time between each bubble.

At box 409, an electric field separates and ionizes the analyte. As an example, the pair of plates 127 and 130 can generate an electric field by having a large potential difference between them.

At box 412, the electric field or a gas flow can transport the analyte for analysis. In one embodiment, a gas is released within chamber 112 to propel the ionized analyte in a predetermined direction. The ionized analyte can be propelled into a mass spectrometer.

At box 415, a mass spectrometer can print the ionized analyte. As an example, the ionized analyte can be applied onto a substrate and deposited onto the substrate. The ionized analyte can be used for plating deposition.

Figure 5:
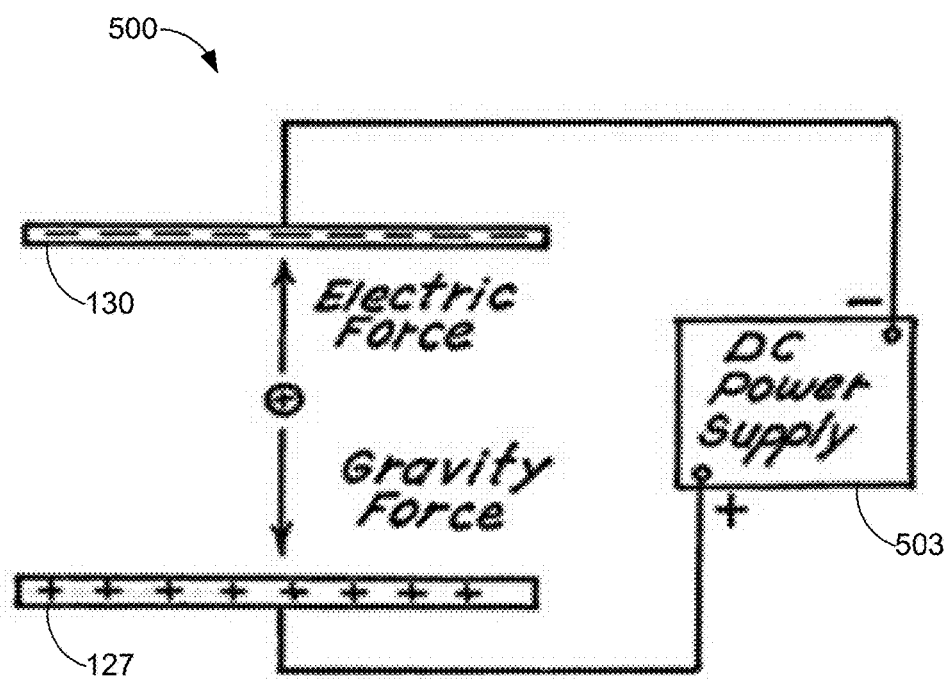
FIG. 5 is a diagram illustrating an example principle involved in the bubble based ion source system.

With reference to FIG. 5, shown is a schematic diagram of a device 500 that illustrates an example of the principle that an electric force being applied upward on a charged drop can balance the force of gravity that applies downwards, such that the drop remains stationary between the two parallel plates 127 and 130. Evaporative loss, however, can cause the drop to rise through the field and deposit itself on the second plate 130. The evaporative loss can also facilitate the transport of both ions and charged droplets in the field and facilitate the transport/drift of ions into a separate analyzer, print region, or charge collection region.

A device 500 capable of generating an appropriate amount of ionized material for analysis in MS via bubble bursting can be dictated by the abilities and limits of a channel that captures and transports the ions. The levitation of an ion using two parallel plates 127 and 130 can allow the jet drop to a hold position while evaporation enables atomization of the ions trapped within the levitating drop.

Figure 6A:
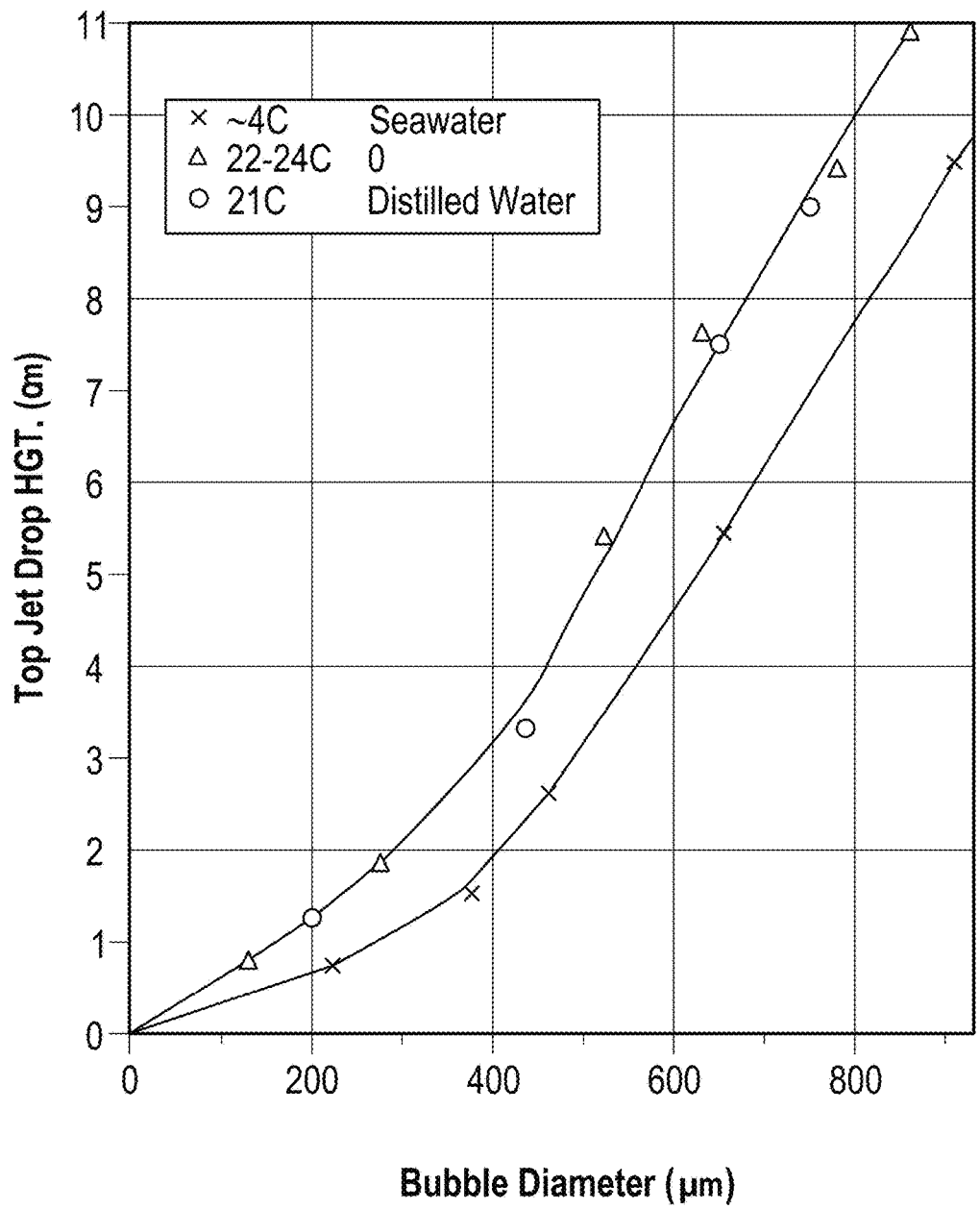
FIGS. 6A-6C and 7A-7D are graphs describing examples of variables related to a bubble size used in the bubble based ion source system.
Figure 6B:
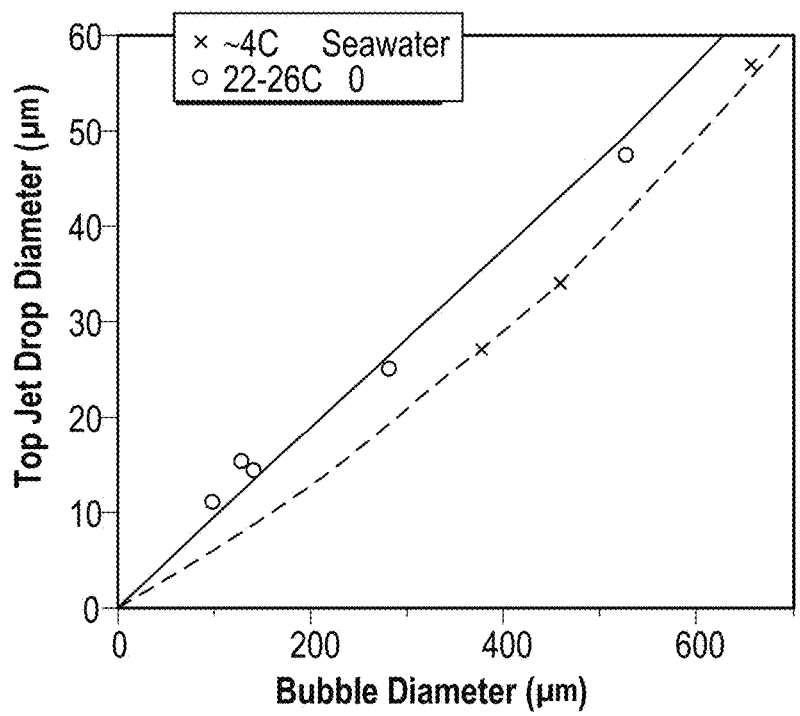
Figure 6C:
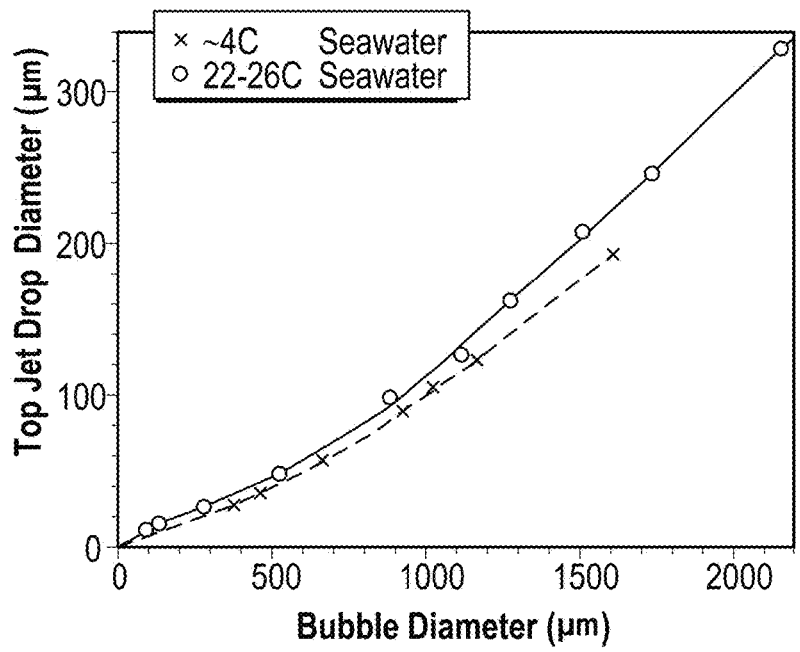
Figure 7A:
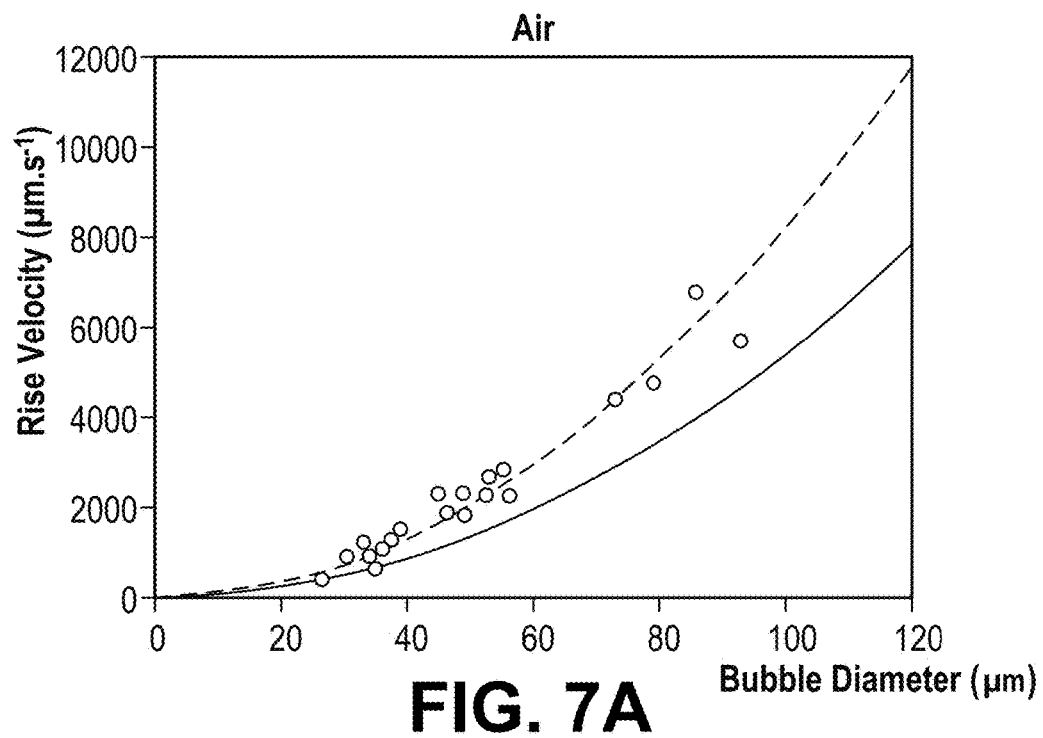
Figure 7B:
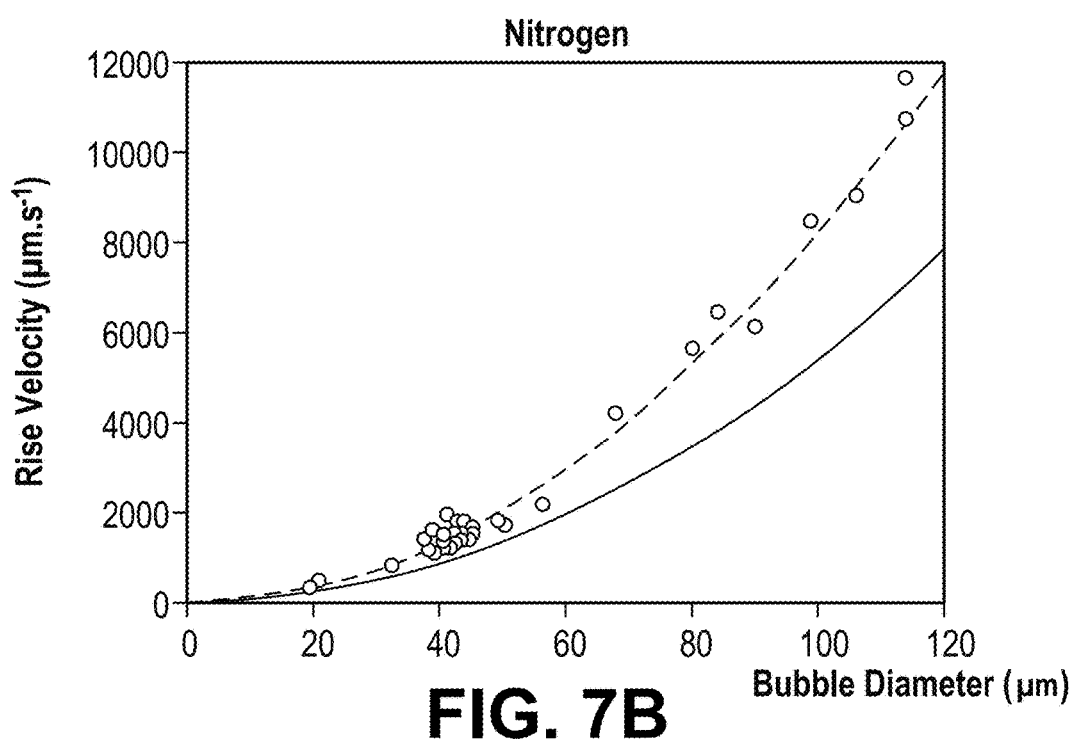
Figure 7C:
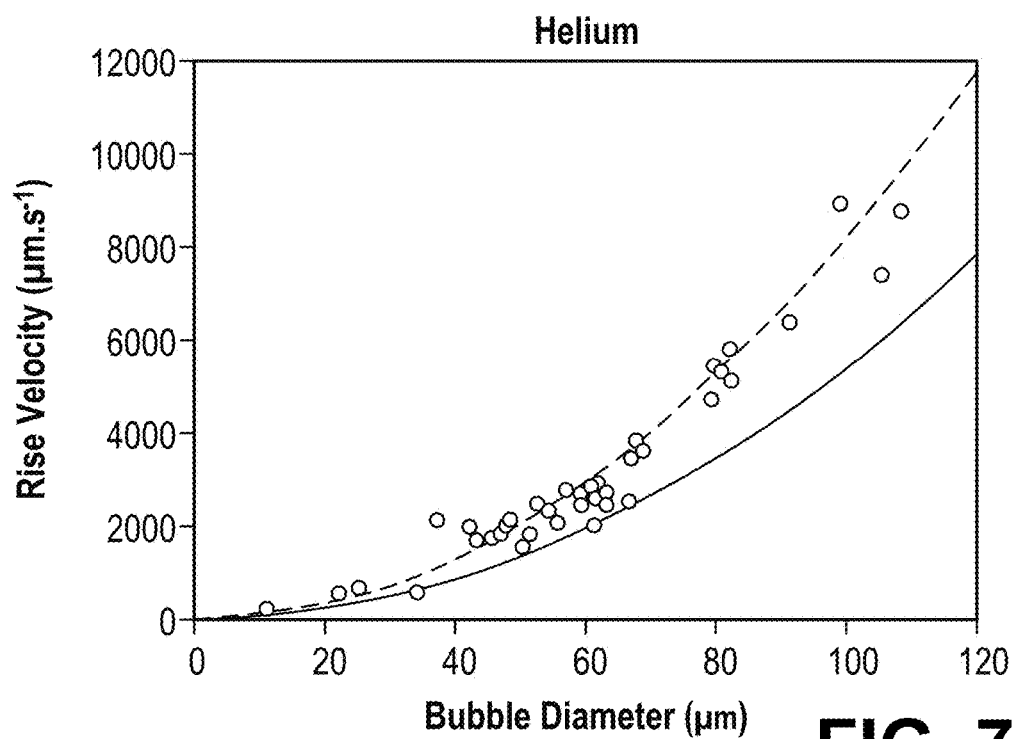
Figure 7D:
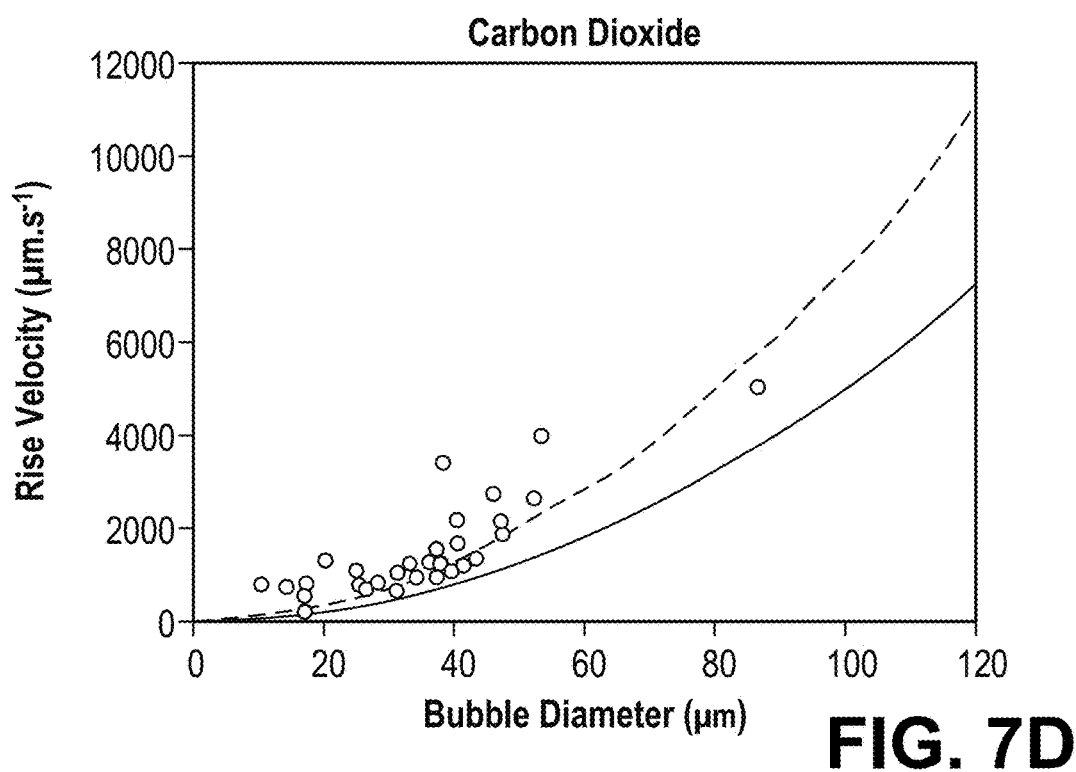

With reference to FIGS. 6A, 6B, and 6C, shown are graphs describing examples of variables related to a bubble size used in the bubble based ion source system 100. In particular, FIG. 6A shows a graph illustrating the relationship between bubble size of a gas bubble 106 and the ejection height, or the height to which the top jet drop 118 is ejected from bubbles bursting in a solution. Similarly, FIGS. 6B and 6C are graphs illustrating the relationship between bubble size of a gas bubble 106 and that of the top jet drop 118 from gas bubbles 106 bursting at seawater at temperatures of about 4° C. and 22°–26° C.

In addition, FIGS. 7A-7D are graphs describing examples of variables related to a bubble size used in the bubble based ion source system 100. Specifically, FIGS. 7A-7D are graphs illustrating terminal rise velocity versus gas bubble 106 diameter for air, Nitrogen, Helium, and Carbon Dioxide bubbles in water, respectively. The solid lines represent Stokes' terminal velocity prediction, and the broken lines represent Hadamard-Rybczynski terminal velocity predictions. Therefore, the graphs shown in FIGS. 7A-7D show comparisons in terminal velocity predictions.

With accompanying control in ion mobility, a sequence of jet drops 118 and associated ions can be collected and transported to detection, deposition, or charge capture devices. At atmospheric pressure, horizontal drift from ambient circulation can be likely to deflect ions from the target. As such, enclosing and minimizing the space around the ionization source and chamber 112 can reduce ion loss. Alternatively, a controlled laminar flow of gas can be utilized to assist evaporation rates and transport to the final device using the ions. Either method of environmental control can use a precise and reproducible formation of jet drops 118 and ejection heights. Otherwise, ion loss to the enclosure boundaries can result. Manipulation of the electric field can occur by controlling the potential energy and the distance between the two plates 127 and 130 both statically and dynamically, using both analog and digital control waveforms and techniques.

Figure 8A:
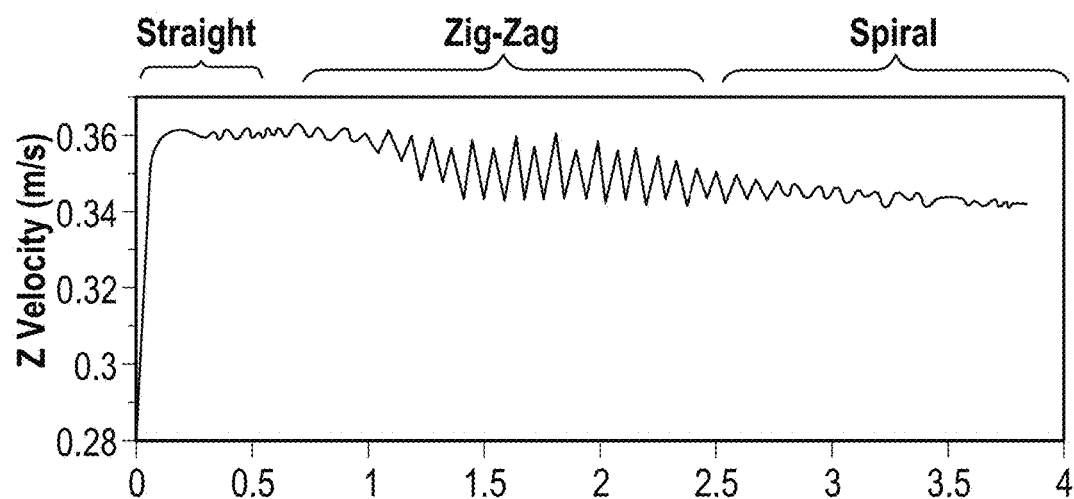
FIGS. 8A-8D are graphs illustrating an example trajectory of a bubble used in the bubble based ion source system.
Figure 8B:
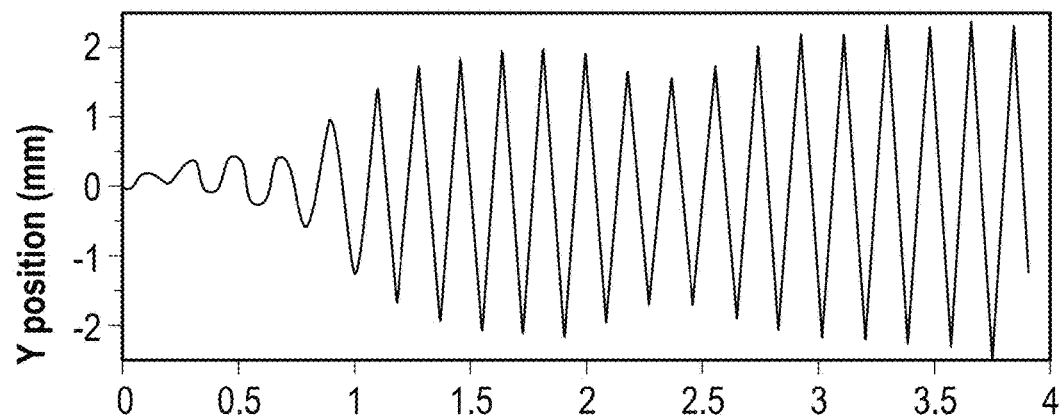
Figure 8C:
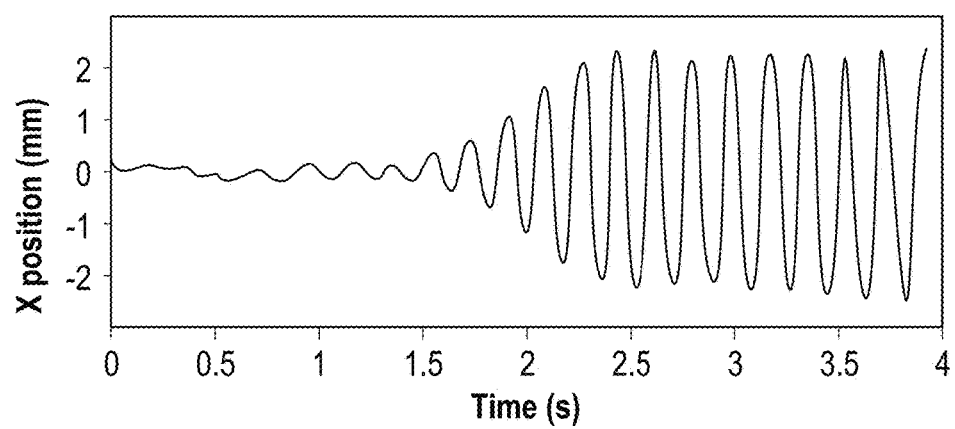
Figure 8D:
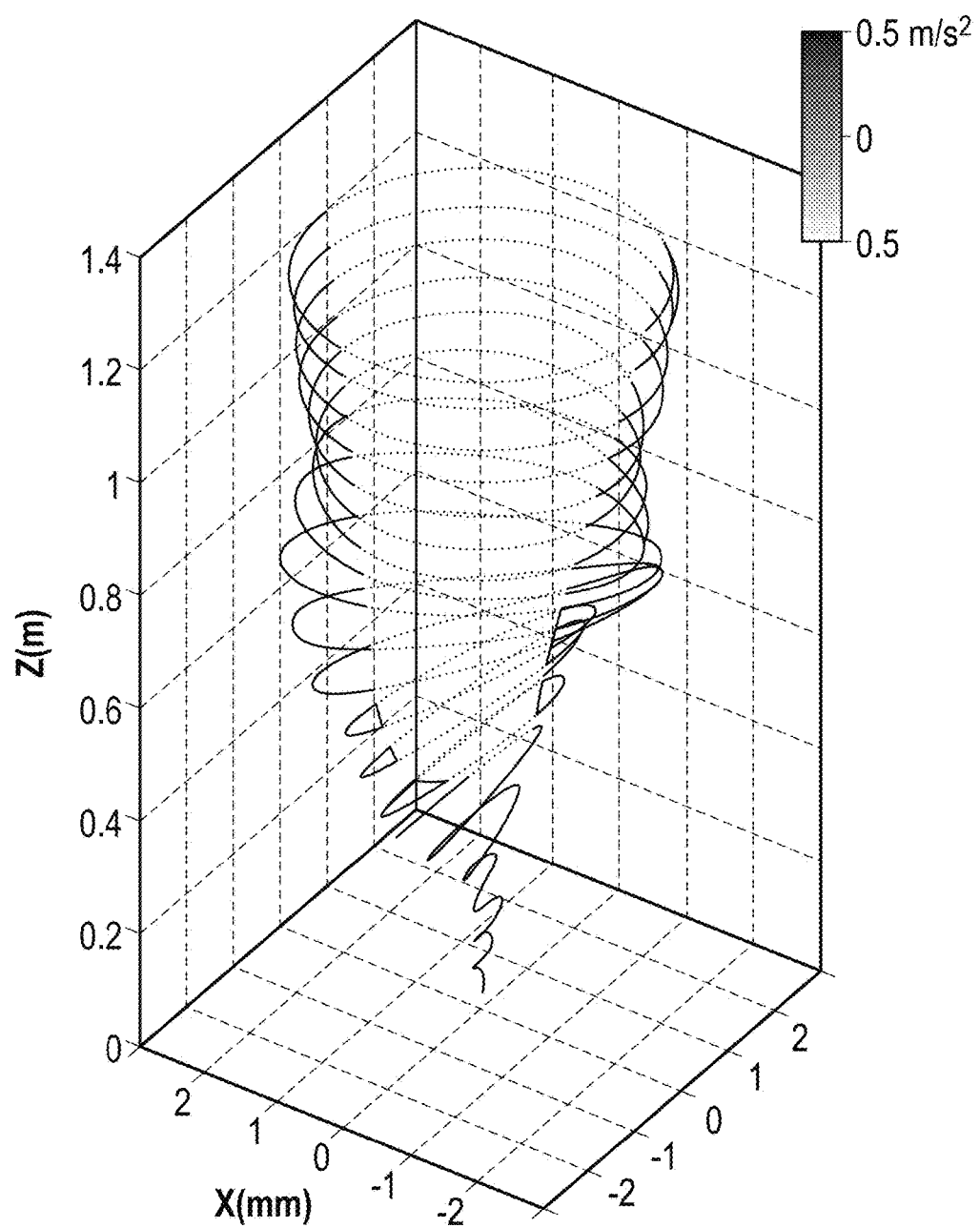

With reference to FIGS. 8A-8D, shown are graphs illustrating an example trajectory of a bubble used in the bubble based ion source system 100. In particular, the graphs shown in FIGS. 8A-8D are graphs describing example trajectories of a gas bubble 106 having about a 1.12 mm radius (at about 1 atm). FIG. 8A shows a vertical z component of velocity as measured with an ultrasound technique. FIG. 8B shows a y position of the gas bubble 106 from camera data, and FIG. 8C shows an x position of the gas bubble 106 from camera data. FIG. 8D shows a three-dimension reconstruction of a full trajectory of the gas bubble 106. In an embodiment, the gas bubble 106 can begin to rise straight, followed by a zigzag motion in various planes with oscillating velocity, and followed by a three-dimensional spiral motion with a steady velocity, as shown in FIG. 8D.

Density and viscosity can affect the ability of a jet drop 118 to be levitated, as does the column height of the sample chamber 112, as described above. Trends in the diameter of the rising gas bubble 106 indicate that larger gas bubbles 106 have a greater rising velocity and can therefore be susceptible to a spiraling trajectory and greater jet drop 118 in height, size, and less precision for the location of the jet drop 118. Ionization of a larger jet drop 118 can require a longer suspension period in the ionization chamber 112 with a greater electric field between plates 127 and 130 for gravitational balance or additional heating from heat source 121. In one embodiment, the gas bubbles 106 are relatively smaller such that the gas bubbles 106 can rise through a sample column less than about 20 cm. In this regard, the gas bubble based ion source can be structured accordingly and accommodate a higher and continuous throughput. The sample column can be structured to be tall enough to allow the gas bubble 106 to scrub sufficient analyte as it rises, but small enough to allow quick flushing and rinsing of the column with clean solvent between samples.

In one embodiment, the bubble ion source can be made at least partially with Printed Circuit Board (PCB) materials and constructions. The use of PCB based MEMS (PCB-MEMS) systems for the creation of fluid transport systems and ion optical systems is provided in U.S. Pat. No. 7,425,276 ("Method for etching microchannel networks within liquid crystal polymer substrates"), which is hereby incorporated by reference in its entirety.

Parallel plate ion chambers can be used for observation of micro-particles by restricting their movements within electric fields. Certain devices can be capable of restricting movement of a 11 μm particle to within 1 μm by applying a 1.2 kV ac to middle electrodes and 7 V dc to the lower plate to counter the effects of gravity and stray electric fields. Keeping the particle stable is essential to making measurements optically or by any other method of observation. However, some embodiments of the ion source comprising an ion trap can allow for the transport of ions from the electric field into any separate operational space. In some embodiments, the multi-plane approach at establishing a trap does not allow for locomotion of the particle.

Figure 9A:
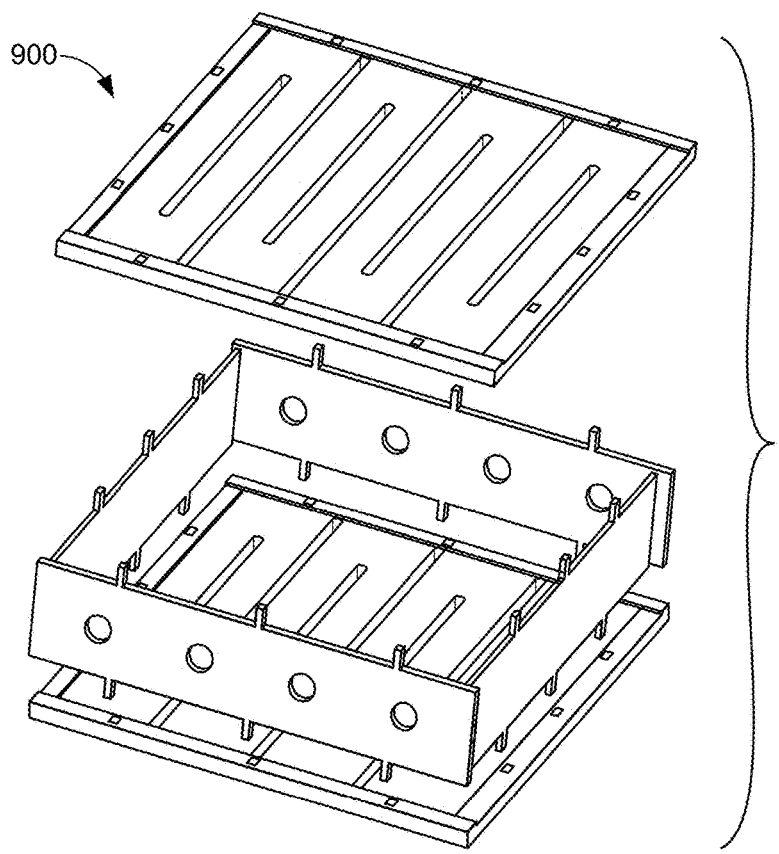
FIGS. 9A and 9B are drawings illustrating an example of a multi-plane ion trap array of the bubble based ion source system.
Figure 9B:
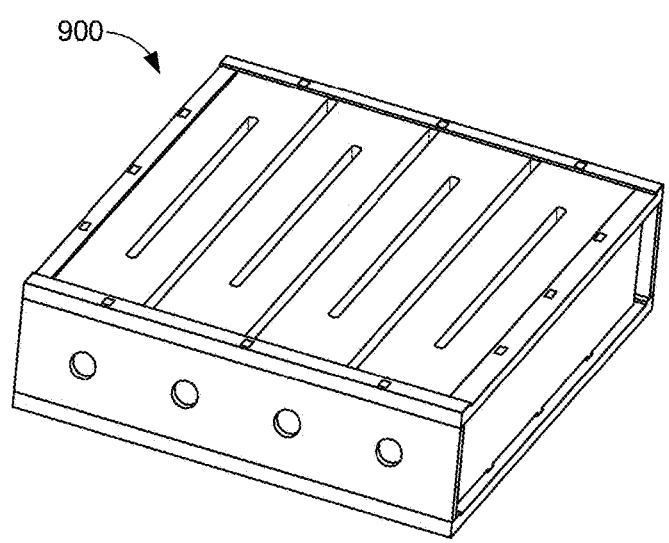

With reference to FIGS. 9A and 9B, shown are drawings illustrating an example of a multi-plane ion channel 900 of the bubble based ion source system 100. In particular, FIG. 9A is a drawing showing one embodiment of the trap channel, also referred to herein as an ion channel or an ion tunnel that comprises a pair of printed circuit board plates (PCB), a pair of end cap electrodes, and a pair of boundary electrodes. In one embodiment, the end cap electrodes and the boundary electrodes are made of stainless steel. In one example, a jet drop 118 can be levitated and ionized between plates 127 and 130 and then transported to the multi-plane ion channel 900 for further transport and/or processing. FIG. 9B is a drawing showing one embodiment of the trap array comprising an Ion Trap Array (ITA) mass analyzer with four channels that can be assembled using three pairs of electrodes. The multi-plane ion channel 900 is one example of a structure that can be used for transporting the volume downstream.

The ion array can comprise strips of conductive material on parallel printed circuit boards for dynamic control of the electric field and can prove useful to transport generated ions from bubble-bursting source. Dynamic control offered by the printed circuit board design offers can facilitate setting the strength of the electric field. In one embodiment, as users of the bubble-bursting ion source choose to use solvents whose charge to mass ratio and ejection heights as jet drops differ from distilled or saline water. In this case, the use of printed circuit board can enable miniaturization and mobility for future designs once the basic configuration has been established.

Figure 10A:
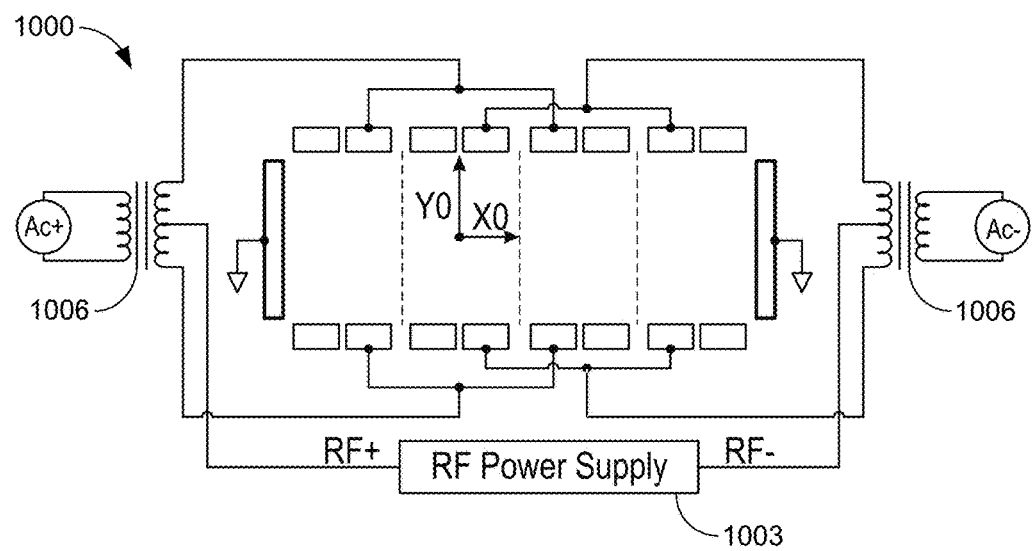
FIG. 10A is an example schematic drawing of the multi-plane ion trap array of FIGS. 9A and 9B.

With reference to FIG. 10A, shown is a schematic drawing 1000 of an example embodiment multi-plane ion trap array, such as the multi-plane ion channel 900 of FIGS. 9A and 9B. In particular, FIG. 10A shows a schematic representation of the ion trap array which can allow longitudinal step-wise translation in the horizontal (x) direction. FIG. 10A shows the connection of a power supply 1003 where signals applied to the adjacent electrodes can have the same potential but opposite polarity. The AC waveforms can be coupled to the RF signal or digital trapping waveform via transformers 1006. The dashed lines shown in FIG. 10A are fields that can keep constant while operating each separate ITA channel.

Figure 10B:
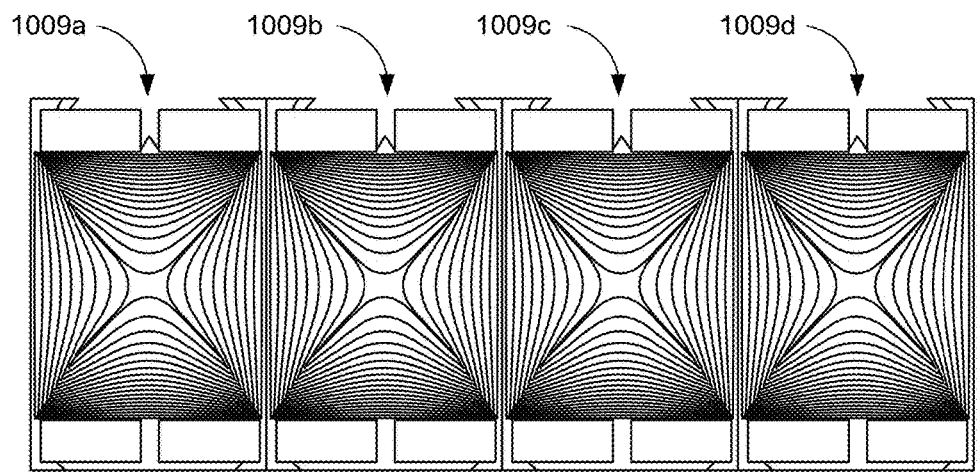
FIG. 10B is a drawing illustrating the electric fields in each channel of an example of the multi-plane ion trap array of FIGS. 9A, 9B, and 10A.

In this regard, FIG. 10B is a drawing 1001 illustrating the electric fields in each channel of an example of the multi-plane ion trap array of FIGS. 9A, 9B, and 10A. Specifically, FIG. 10B shows electric fields in a first channel 1009a, a second channel 1009b, a third channel 1009c, and a fourth channel 1009d of the ITA. In one embodiment, the dimensions of each channel of the ITA is about x=5.5 mm and about y=6.25 mm. Each of the channels 1009a-d is an ion trap, where the ion can be trapped in a center of each channel 1009a-d. The channels 1009a-d can modulate ions and get a mass spectrum from the ions. In some embodiments, a button electrode levitation chamber (BEL) can for the levitation of a charged particle below the level of the truncated, vertically oriented quadrupoles yet laterally centered among the poles.

Figure 11A:
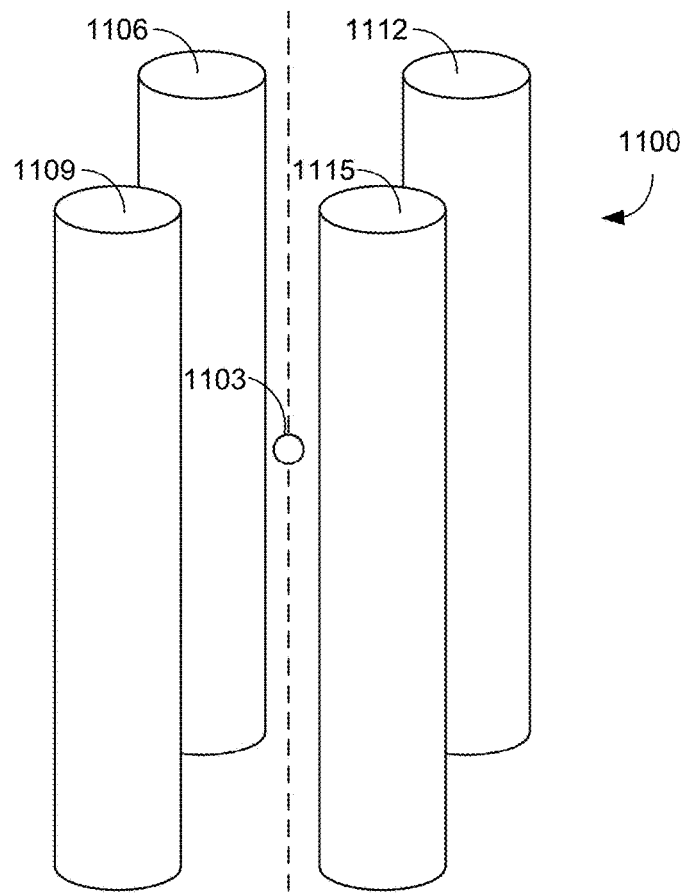
FIGS. 11A-11C are diagrams illustrating an example of a button electrode levitation chamber of the bubble based ion source system.
Figure 11B:
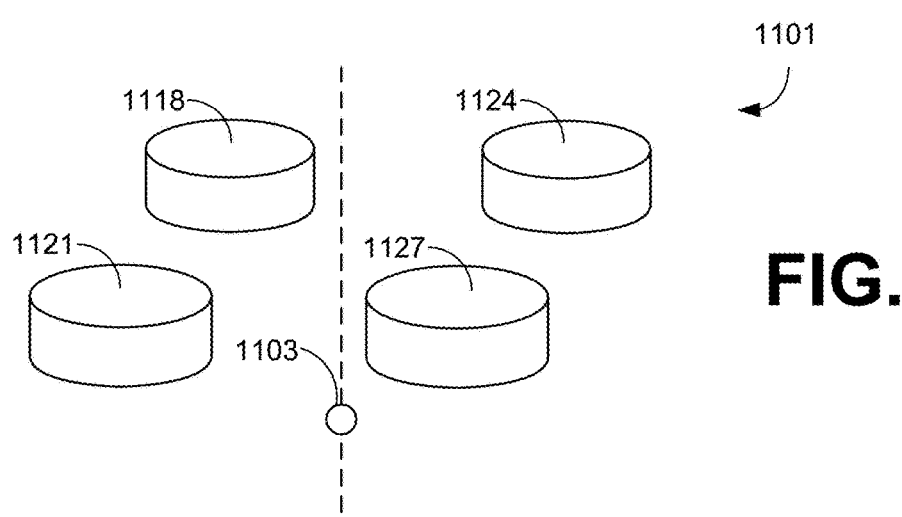

With reference to FIG. 11A, shown is an example schematic 1100 that depicts a standard quadrupole electrode that levitates particles 1103 between the four pole electrodes 1106, 1109, 1112, and 1115. FIG. 11B shows an example schematic that depicts the BEL design in which the particle 1103 levitates below the shortened button electrodes 1118, 1121, 1124, and 1127. Such orientation could allow for the proper evaporation and ultimate ionization of charged water jet drops 118.

Figure 11C:
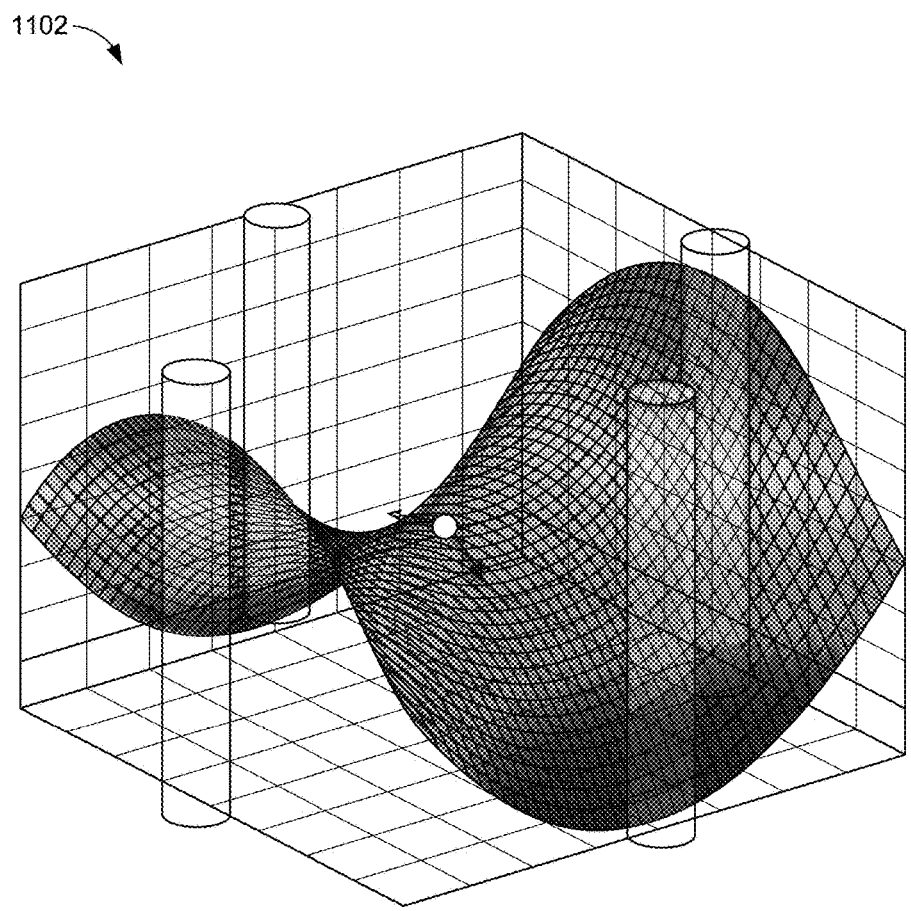

With reference to FIG. 11C, shown is a graph 1102 illustrating the three-dimensional potential function calculated for an ideal quadrupole trap where a hypothetical particle is shown as a white circle located at the null point and the arrows represent the instantaneous unstable directions. Alternating the polarity of the electrodes shifts the electric fields in such a way to create a saddle where electric forces balance gravitational forces. As a particle begins to fall off a low point of the saddle, the electric fields shift to rotate the saddle to trap the particle. In one embodiment, induced gaseous flow could be the mechanism by which to transport ions to the analytical column.

Embodiments of the bubble based ion source may comprise an ion channel configured to transport generated ions into any existing MS. A pressure gradient can be utilized similar to existing arrangements with ambient pressure ion sources to introduce the ions to the MS. Electrodynamic ion funnels or a variation of ion optics can facilitate the transmission of ions through the path of the instrument rather than loss of ions against interior surfaces. In one embodiment, a series of annular electrodes of decreasing radius can be employed to successfully make the introduction from atmospheric pressure into a low pressure environment. In an experiment conducted where each drop was measured, about 40 ions were detected in each jet drop 118.

Figure 12A:
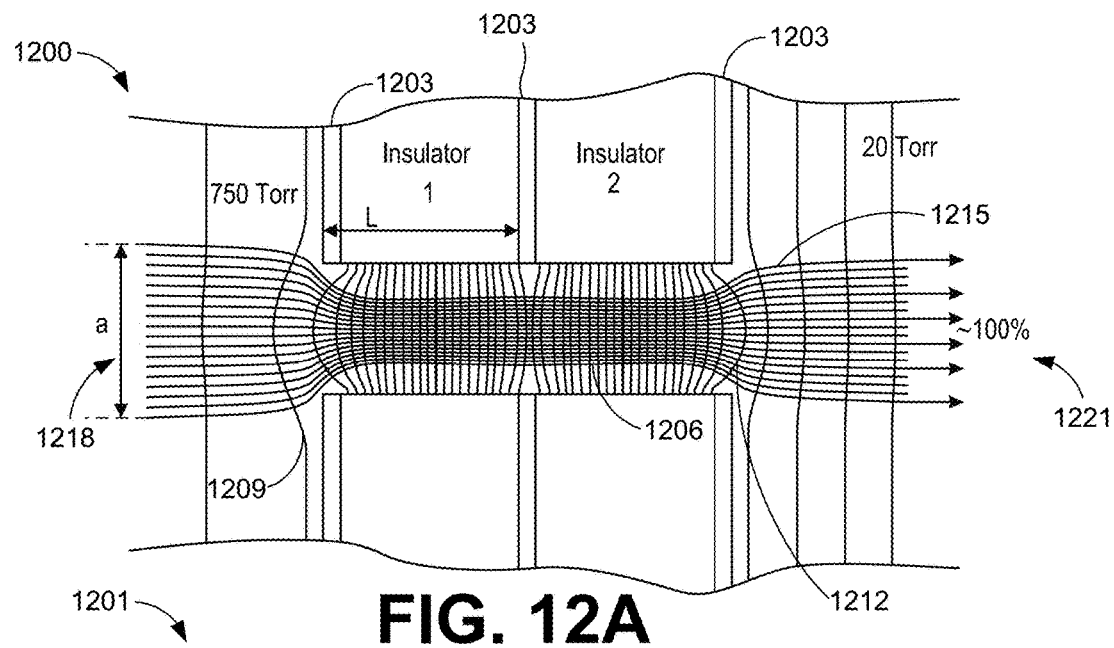
FIGS. 12A and 12B are drawings and photos illustrating the use of micro ion-optical systems technology in the bubble based ion source system.

With reference to FIG. 12A, shown is an example embodiment of a multilayer ion channel 1200 using Micro Ion-Optical Systems Technology (MIST) according to various embodiments. The multilayer ion channel 1200 can include shaped electrodes 1203 along with orifice arrays for the sampling and transport of ions into separate regions/zones. The shaped electrodes 1203 can be separated by insulators to generate an electric field 1206. In some embodiments, the bubble based ion source system 100 includes the multilayer ion channel 1200.

The multilayer ion channel 1200 can be configured to transport jet drops 118 ions that are levitated and ionized in chamber 112. Element 1209 shows equipotential lines from the multilayer ion channel. If the uniform field is employed at element 1212 then the strength is limited by low pressure breakdown. Element 1215 shows an ion trajectory within the multilayer ion channel 1200.

The multilayer ion channel 1200 can include an entrance 1218 that includes an aperture with an opening size of "a" as shown. The pressure at the entrance 1218 can be a standard atmospheric pressure, for example 750 Torr. The entrance 1218 can be positioned to pull ions from the chamber 112. A vacuum is applied at an exit 1221. The pressure at the exit 1221 can be substantially lower than entrance 1218. As an example, the pressure at the exit 1221 can be 20 Torr.

Jet drops 118 can enter at the entrance 1218 and be pulled into the multilayer ion channel 1200 by one or more of the electric field and a flow through the multilayer ion channel 1200 caused by the pressure difference. Once the jet drops 118 reach the exit 1221, the energy of the jet drops 118 are damped such that a path of the jet drops 118 are dominated by the field lines of the electric field.

A MIST can be used to fabricate ion optical elements for the multilayer ion channel 1200. MIST is the convergence of fluidic-electrostatic-mechanical functions into an active or passive system for ion manipulation and control using controlled, shaped electric fields and controlled fluidics. The system can be in package (SIP) or system on a chip (SOC). Active systems can dynamically control fields and flow and contain moving mechanical components. Passive systems have no moving parts and can be easier to reduce cost effectively. Embodiments of the bubble based ion source that comprises the PCB MIST can include adaptive sampling of ions, laminated 3D systems, feedback control of ion transmission, integration of electronics and large area designs.

In one embodiment, the ion optical elements can be used to increase the focusing of ions from the atmospheric ion generation zone into the very small differential pumping apertures at the interface of separate analyzer, deposition, or collection system. The divergent ion source of a bubble ion generation can result in an increase in ion transport into and away from the ion generating zone by a factor of three to ten. Additionally, an entire integrated ion source with electrical circuits/components, ion optical elements and fluidics can be made using PCB/PCBMEMS.

Figure 12B:
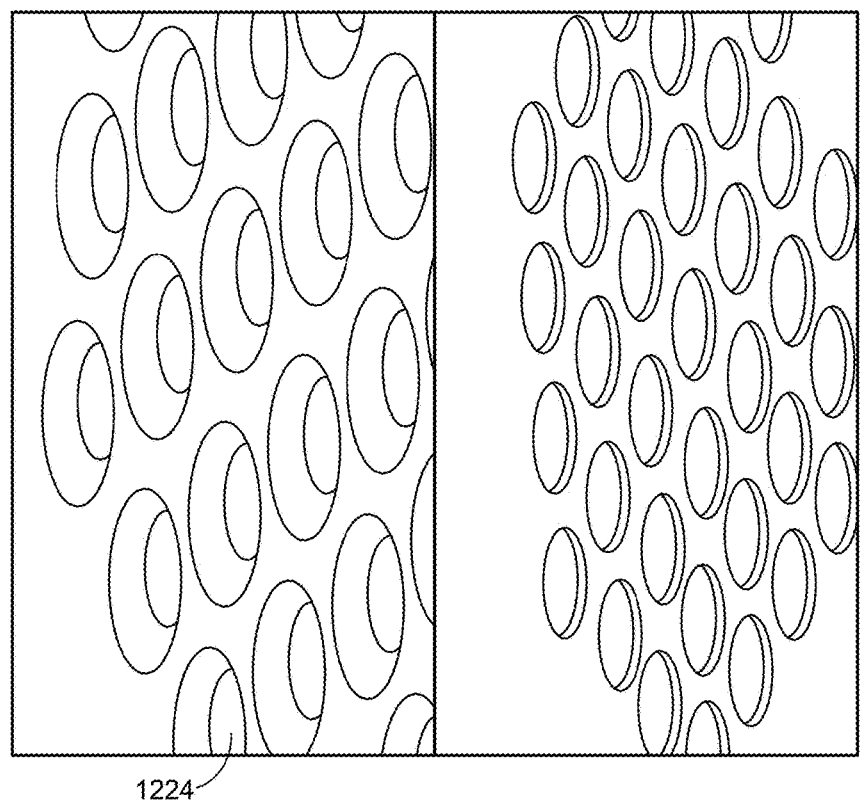

With reference to FIG. 12B, shown is an array of orifices 1201 of multilayer ion channels 1200. Each of the orifices 1224 in the array of orifices 1201 can be an entrance 1218 of a different multilayer ion channel 1200. The array of orifices 1201 can transport a greater quantity of jet drops 118. As an example, an array of bubble generators 103 can each generate multiple bubbles to create jet drops 118 that are levitated and ionized in chamber 112. In this example, the array of orifices 1201 can facilitate transport of the numerous ionized jet drops 118 that are generated.

Figure 13:
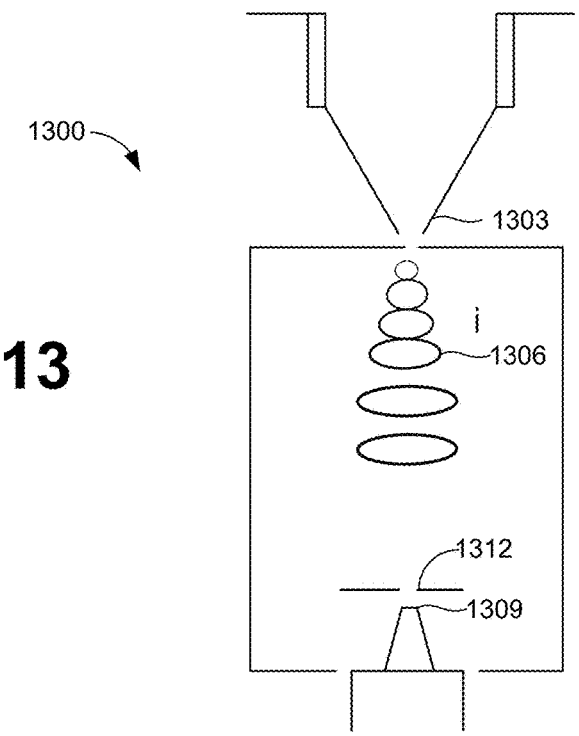
FIG. 13 is an example schematic of a vertically oriented atmospheric pressure ion sampling ion channel, ion source, and associated electrode.

With reference to FIG. 13, shown is an example schematic of the vertically oriented atmospheric pressure ion sampling ion channel 1300 that includes a sampling orifice 1303, ion source 1306, and associated electrode 1309. The ion source 1306 can include multiple jet drops 118 that expand as they pass toward the electrode 1309. In one embodiment, the jet drops 118 are ions created by ionizing an analyte as described herein. The electrode 1309 can include an aperture 1312.

Figure 14:
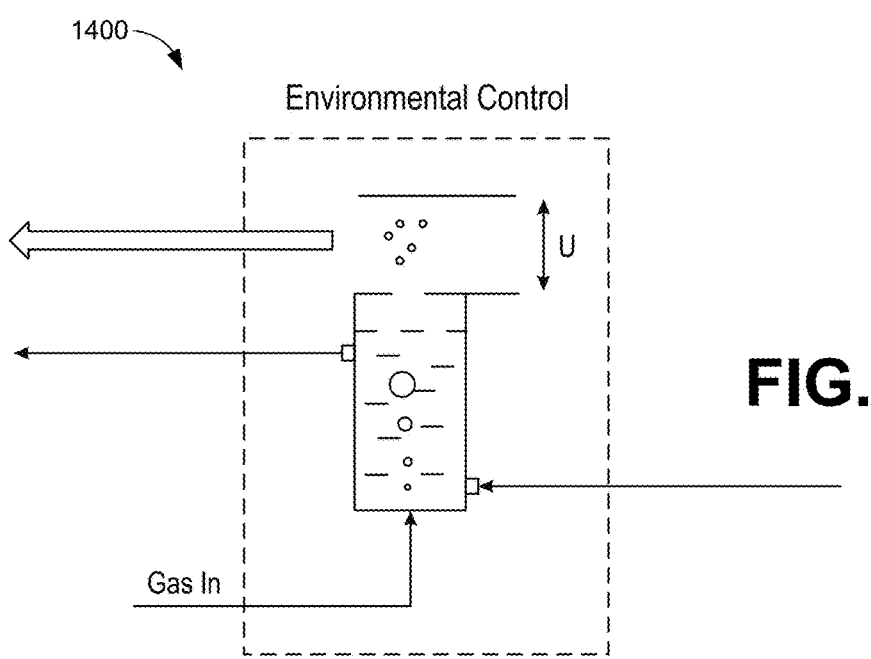
FIG. 14 is an example schematic of one embodiment of the bubble based ion source system.

With reference to FIG. 14, shown is an example bubble bursting ion source system schematic 1400 with controls on the environment including, but not limited to, gas flow, solvent flow, field strength, and/or any other portion of the system that can be controlled. In this way, the upstream options that may be available to the end user can be selection of gas type, the solvent type, field strength, heating, and flow rates of bubbled gas or of gas transport. The system will have to be contained to reduce external environmental interference yet limit the influence of internal turbulence or ion formation and transport. Multiple bubbles can be generated as shown in FIG. 14 to create a parallel charged particle source.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y.'"

Therefore, at least the following is claimed:

1. A bubble based ion source system comprising:
an ion source configured to generate a plurality of ions comprising:
a container at least partially comprising a solvent;
a bubble generator coupled to the container configured to generate a plurality of bubbles within the solvent; and
an ion channel comprising an aperture and an electrode, the ion channel configured to receive the plurality of ions through the aperture, the plurality of ions being generated based at least in part on at least a portion of the solvent from at least one of the plurality of bubbles.

2. The bubble based ion source system of claim 1, wherein the electrode is configured to facilitate guiding the plurality of ions to an analyzer device.

3. The bubble based ion source system of claim 2, wherein the analyzer device is at least one of: an ion mobility spectrometer, a mass spectrometer, a charged particle deposition system, or a charge energy generation device.

4. The bubble based ion source system of claim 1, wherein at least one voltage applied to the ion channel facilitates moving the plurality of ions into an analyzer device.

5. The bubble based ion source system of claim 1, further comprising a heat source positioned above the container, wherein the plurality of ions are generated further based at least in part on the heat source.

6. The bubble based ion source system of claim 1, wherein the bubble generator is configured to generate the plurality of bubbles within the solvent by injecting air into the solvent.

7. An atmospheric ion source generator comprising:
a container at least partially enclosing a solvent;
a bubble generator configured to generate a plurality of bubbles within the solvent, the plurality of bubbles move to a surface of the solvent when generated; and
an ion channel configured to receive a plurality of ions, the plurality of ions being generated based at least in part on at least a portion of the solvent from at least one of the plurality of bubbles.

8. The atmospheric ion source generator of claim 7, wherein the plurality of ions are drawn through a plurality of apertures in an array of ion channels.

9. The atmospheric ion source generator of claim 8, wherein the array of ion channels comprises the ion channel.

10. The atmospheric ion source generator of claim 7, wherein each of the bubbles burst in a form of a jet drop, and at least a portion of the jet drop is received through an aperture.

11. The atmospheric ion source generator of claim 7, wherein the ion channel comprises an electrode that applies a voltage to the ion channel that facilitates keeping the plurality of ions stabilized within the ion channel without touching walls of the ion channel.

12. The atmospheric ion source generator of claim 7, wherein the ion channel comprises a button electrode levitation chamber to facilitate keeping the plurality of ions stabilized within the ion channel without touching walls of the ion channel.

13. The atmospheric ion source generator of claim 7, wherein the ion channel comprises a plurality of planes to facilitate translation of the plurality of ions horizontally.

14. A method of generating ions comprising:
generating, via a bubble generator, a plurality of bubbles in a solvent, the plurality of bubbles rising to a surface of the solvent; and
receiving, via an ion channel, a plurality of ions through an aperture, the plurality of ions being generated based at least in part on at least a portion of the solvent from at least one of the plurality of bubbles.

15. The method of generating ions of claim 14, guiding the plurality of ions to an analyzer device based at least in part on a voltage applied to the ion channel.

16. The method of generating ions of claim 15, wherein the voltage is based at least in part on a configuration of the ion channel and a desired field strength.

17. The method of generating ions of claim 16, further comprising applying a second voltage to one of a plurality of layers of the ion channel, wherein the voltage is applied to another one of the plurality of layers of the ion channel.

18. The method of generating ions of claim 16, wherein the plurality of ions are guided to the analyzer device based at least in part on a plurality of voltages applied to a plurality of layers of the ion channel, wherein the voltage is one of the plurality of voltages and the voltage is applied to one of the plurality of layers of the ion channel.

19. The method of generating ions of claim 14, generating the plurality of ions by evaporating the at least a portion of the solvent from the at least one of the plurality of bubbles.

20. The method of generating ions of claim 14, wherein each of the bubbles burst at the surface of the solvent in a form of a jet drop which is received through the aperture of the ion channel.

* * * * *